(12) United States Patent
Lauer et al.

(10) Patent No.: US 7,398,255 B2
(45) Date of Patent: Jul. 8, 2008

(54) NEURAL PROSTHESIS WITH FUZZY LOGIC CONTROL SYSTEM

(75) Inventors: Richard Lauer, Abington, PA (US); Brian T. Smith, Hatboro, PA (US); Randal R. Betz, Langhorne, PA (US)

(73) Assignee: Shriners Hospitals for Children, Tampa, FL (US)

( * ) Notice: Subject to any disclaimer, the term of this patent is extended or adjusted under 35 U.S.C. 154(b) by 286 days.

(21) Appl. No.: 11/158,923

(22) Filed: Jun. 22, 2005

(65) Prior Publication Data
US 2006/0015470 A1 Jan. 19, 2006

Related U.S. Application Data

(60) Provisional application No. 60/587,980, filed on Jul. 14, 2004.

(51) Int. Cl.
*G06F 15/18* (2006.01)
*A61F 2/72* (2006.01)

(52) U.S. Cl. .................. 706/8; 706/1; 706/22; 623/25; 623/24

(58) Field of Classification Search ...................... 706/8, 706/1, 22; 623/25, 24
See application file for complete search history.

(56) References Cited

U.S. PATENT DOCUMENTS

| | | | |
|---|---|---|---|
| 5,748,845 | A | 5/1998 | Labun |
| 6,163,725 | A | 12/2000 | Peckham |
| 6,424,868 | B1 * | 7/2002 | Smith et al. ................... 607/59 |
| 6,633,783 | B1 * | 10/2003 | Dariush et al. ................ 700/50 |
| 2004/0093093 | A1 * | 5/2004 | Andrews ....................... 623/25 |

OTHER PUBLICATIONS

Richard Lauer, Brian Smith, Randal Betz, James McCarthy. "An Adaptive Neuro-Fuzzy Control Algorithm for Electrically Stimulated Gait in the Child with Cerebral Palsy", NIH Neural Prosthesis Workshop, Oct. 16-18, 2002.*

Richard Lauer, Brian Smith, Dan Coiro, Randal Betz, James McCarthy. "Feasibility of Gait Event Detection Using Intramuscular Electromyography in the Child with Cerebral Palsy", International Neuromodulation Society, Neuromodulation, vol. 7, No. 3, Jul. 2004, pp. 205-213.*

Margaret M. Skelly, Howared Jay Chizeck. "Real-Time Gait Event Detection for Paraplegic FES Walking", IEEE Transactionson Neural Systems and Rehabilitation Engineering, vol. 9, No. 1. Mar. 2001, pp. 59-68.*

Richard Lauer, Brian Smith, James McCarthy. "An Adaptive Neuro-Fuzzy Control Algorithm for Electrically Stimulated Gait in the Child with Cerebral Palsy", NIH Neural Prosthesis Workshop, Oct. 16-18, 2002.*

(Continued)

*Primary Examiner*—Joseph P. Hirl
*Assistant Examiner*—Adrian L Kennedy
(74) *Attorney, Agent, or Firm*—Fish & Richardson P.C.

(57) ABSTRACT

A neural prosthesis for providing a signal indicative of a predicted event from a cycle of events includes a signal-acquisition system for receiving a neural signal, and a fuzzy-logic inference system for receiving, from the signal acquisition system, a signal indicative of a current location within the cycle of events. The fuzzy-logic inference system is configured to predict a successive event in the cycle of events.

20 Claims, 8 Drawing Sheets

OTHER PUBLICATIONS

Lauer et al., "Applications of a Neuro-fuzzy Network for Gait Event Detection Using Electromyography in the Child with Cerebral Palsy," Abstract, NIH Neural Prosthesis Workshop, Oct. 16-18, 2002.

Lauer et al., "An Adaptive Neuro-Fuzzy Control Algorithm for Electrically Stimulated Gait in the Child with Cerebral Palsy," Proceedings of the 9th Annual Conferences of the International Functional Electrical Stimulation Society (IFESS), Jul. 1-5, 2003.

Smith et al., "Evaluation of Force-Sensing Resistors for Gait Event Detection to Trigger Electrical Stimulation to Improve Walking in the Child With Cerebral Palsy", Transactions on Neural Systems and Rehabilitation Engineering, vol. 10, No. 1, Mar. 2002, pp. 22-29.

Williamson et al., "Gait Event Detection for FES Using Acceleromaters and Supervised machine Learning," IEEE Transactions on Rehabilitation Engineering, vol. 8, No. 3, Sep. 2000, pp. 312-319.

Skelly et al., "Real-Time gait Event Detection for Paraplegic FES Walking," IEEE Transactions on Neural Systems and Rehabilitation Engineering, vol. 9, No. 1, Mar. 2001, pp. 59-68.

Micera et al., "Neuro-Fuzzy Extraction of Angular Information from Music Afferents for Ankle Control during Standing in Paraplegic Subjects: an Aninmal Model," IEEE Transactions on Biomedical Engineering, vol. 48, No. 7, Jul. 2001, pp. 787-405.

Graupe et al., "Artificial Neural network Control of FES in Paraplegics for Patient Responsive Ambulation," IEEE Transactions on Biomedical Engineering, vol. 42, No. 7, Jul. 1995, pp. 699-707.

Au et al., "EMG-Based Protection of Shoulder and Elbow Kinematics in Able-Bodied and Spinal Cord Injured Individuals," IEEE Transactions on Rehabilitation Engineering, vol. 8, No. 4, Dec. 2000, pp. 471-480.

Lauer et al., "Feasibility of Gait Event Detection using Intramuscular Electromyography in the Child with Cerebral Palsy," International Neuromodulation Society, Neuromodulation, vol. 7, No. 3, 2004, pp. 205-213.

* cited by examiner

|  |  | SUBJECT 1 (FIS) | SUBJECT 1 (FIS & CONTROLLER) | SUBJECT 2 (FIS) | SUBJECT 2 (FIS & CONTROLLER) |
|---|---|---|---|---|---|
| WA | CORRECT | 85.3 | 87.8 | 27.2 | 49.4 |
|  | TRANSITION | 13.9 | 12.2 | 38.9 | 28.5 |
|  | ERROR | 0.9 | 0.0 | 33.9 | 22.1 |
| MSt | CORRECT | 41.7 | 67.7 | 35.8 | 56.9 |
|  | TRANSITION | 54.5 | 32.1 | 49.5 | 35.8 |
|  | ERROR | 3.8 | 0.2 | 14.7 | 7.4 |
| TSt | CORRECT | 86.0 | 91.7 | 54.8 | 66.3 |
|  | TRANSITION | 10.8 | 8.0 | 43.6 | 33.7 |
|  | ERROR | 3.2 | 0.3 | 1.7 | 0.0 |
| PSw | CORRECT | 74.0 | 79.7 | 44.8 | 59.3 |
|  | TRANSITION | 22.3 | 20.3 | 54.0 | 40.4 |
|  | ERROR | 3.0 | 0.0 | 1.2 | 0.3 |
| ISw | CORRECT | 83.5 | 90.0 | 38.2 | 70.5 |
|  | TRANSITION | 12.3 | 10.0 | 54.5 | 29.5 |
|  | ERROR | 4.2 | 0.0 | 7.3 | 0.0 |

FIG. 5

|  | WA (ms) | MSt (ms) | TSt (ms) | PSw (ms) | ISw (ms) |
|---|---|---|---|---|---|
| SUBJECT 1 (FIS) | 25.3 ± 22.2 | 16.3 ± 50.7 | 132.6 ± 64.8 | 51.3 ± 21.8 | 71.1 ± 36.4 |
| SUBJECT 1 (FIS & CONTROLLER) | 29.6 ± 24.2 | 79.9 ± 44.8 | 154.0 ± 61.2 | 52.9 ± 21.2 | 81.8 ± 34.4 |
| SUBJECT 2 (FIS) | -46.1 ± 48.3 | -78.4 ± 52.0 | 46.5 ± 67.3 | 12.5 ± 23.0 | -16.5 ± 41.9 |
| SUBJECT 2 (FIS & CONTROLLER) | -19.8 ± 49.2 | -32.6 ± 61.1 | 78.7 ± 72.8 | 25.9 ± 24.7 | 35.2 ± 38.3 |

FIG. 6

NEURAL PROSTHESIS WITH FUZZY LOGIC CONTROL SYSTEM

RELATED APPLICATIONS

This application claims priority under 35 U.S.C. §119 from U.S. Provisional Patent Application No. 60/587,980, filed Jul. 14, 2004, the contents of which are incorporated herein by reference.

FIELD OF INVENTION

The invention relates to neural prostheses, and in particular, to controlling stimulation of muscle contraction.

BACKGROUND

The process of walking is a sequence of steps, each of which is characterized by certain landmark events. These landmark events are often referred to as "gait events." The five gait events most often used in the analysis of gait are: weight acceptance ("WA"), mid-stance ("MSt"), terminal stance ("TSt"), pre-swing ("PSw"), and initial swing (ISw"). These events are described in detail by Perry, "Gait Analysis: Normal and Pathological Function," Delmar Thomson Learning, Clifton Park, N.Y., 1992, the contents of which are incorporated herein by reference in their entirety.

The time between gait events may be short, as in a brisk walk, or it may be long, as in a leisurely stroll. However, regardless of the time interval between them, these gait events are expected to occur in the same order. Moreover, the time intervals between gait events are expected to be related. For example, if the interval between pre-swing and initial swing is short, then the interval between terminal stance and pre-swing should also be short, otherwise the gait will degenerate into a sequence of lurches.

When walking, the legs move into positions that are appropriate for each gait event. To carry this out requires cooperation between muscles, which move the legs, and nerve impulses, which trigger the muscles into contracting at appropriate times. In persons afflicted with cerebral palsy, the muscles are available, but the nerve signals either do not arrive, or they do not arrive at the correct times.

SUMMARY

The invention is based in part on the recognition of the effectiveness of fuzzy logic systems at predicting landmark events in repetitive physiological processes.

In one aspect, the invention includes a neural prosthesis for providing a signal indicative of a predicted event from a cycle of events. The neural prosthesis includes a signal-acquisition system for receiving a neural signal and a fuzzy-logic inference system for receiving, from the signal acquisition system, a signal indicative of a current location within the cycle of events. The fuzzy-logic inference system is configured to predict a successive event in the cycle of events.

Certain embodiments of the neural prosthesis further include a supervisory controller for receiving an output of the fuzzy-logic inference system. The supervisory controller includes a memory for storing data indicative of at least one preceding predicted event in the cycle of events, and a comparator to impose constraints on the successive event at least in part on the basis of the preceding predicted event.

The comparator can be configured to implement a rule requiring that the successive event be selected in a manner consistent with an order of events in the cycle. Or, the comparator can be configured to implement a rule requiring that the successive event be consistent with a preceding event of the cycle.

In some embodiments, an additional fuzzy-logic inference system is configured to provide, at least in part on the basis of an output received from the comparator, a signal indicative of a predicted event.

Alternative embodiments of the invention include those having a stimulus delivery system in communication with the fuzzy-logic inference system. The stimulus delivery system in such embodiments is configured to generate a stimulating signal at least in part on the basis of a signal indicative of a predicted event.

Some embodiments are adapted to receive, as the neural signal, an EMG signal. In these embodiments, the signal-acquisition system includes electrodes for receiving an electro-myographic signal. Such electrodes can be surface mounted electrodes or implantable electrodes.

Embodiments of the invention also include those in which the fuzzy inference system is an adaptive neuro-fuzzy inference system.

In another aspect, the invention includes a neural prosthesis for providing a signal predicting a successive gait event. The neural prosthesis includes a signal-acquisition system for receiving a neural signal and a first fuzzy-logic inference system for receiving a signal from the signal acquisition system. The first fuzzy-logic inference system is configured to predict a candidate successive event at least in part on the basis of the signal. A supervisory controller receives data indicative of the candidate successive event from the first fuzzy-logic inference system. The supervisory controller includes a memory for storing data indicative of a preceding predicted gait event provided by the first fuzzy-logic inference system and a comparator to impose constraints on a successive gait event at least in part on the basis of the preceding predicted gait event. A neural stimulator is in communication with the supervisory controller. The neural stimulator is configured to generate a stimulating signal at least in part on the basis of the signal indicative of the predicted event.

Additional embodiments include those having a second fuzzy-logic inference system configured to provide, at least in part on the basis of an output received from the comparator, a signal indicative of a predicted event.

In yet other embodiments, the first fuzzy-logic inference system is an adaptive neuro-fuzzy inference system.

In another aspect, the invention includes a method for providing a signal indicative of a predicted event from a cycle of events. The method includes receiving a neural signal indicative of a current location within the cycle of events and applying a fuzzy-logic inference algorithm to the neural signal. Optionally, the method can also include predicting a successive event in the cycle of events on the basis of an output of the fuzzy-logic inference algorithm.

The fuzzy-inference algorithm can be any of a variety of types. For example, it can be a Sugeno type algorithm, or an adaptive neuro-fuzzy inference algorithm.

Among various practices of the invention are those in which data indicative of at least one preceding predicted event in the cycle of events is stored. A constraint is then identified on the basis of the preceding predicted event. This constraint is imposed on the successive event. Identification of a constraint can include, for example, requiring that the successive event be selected in a manner consistent with an order of events in the cycle, or requiring that the successive event be consistent with a preceding event of the cycle.

Other practices of the invention are those that include the reception of an output indicative of the successive event following imposition of the constraint thereon. An additional fuzzy-logic algorithm is then applied to the output to provide a signal indicative of a predicted event.

Yet other practices of the invention include those in which a stimulus signal is generated at least in part on the basis of a signal indicative of a predicted event.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

BRIEF DESCRIPTION OF THE FIGURES

FIGS. 5 and 6 are tables showing experimental results corresponding to FIG. 4.

DETAILED DESCRIPTION

A person afflicted with cerebral palsy generally has control over the upper muscles of the leg, but not of the lower ones. As a result, when such a person walks, the lower portion of the leg often fails to keep up with the motion of the upper portion.

Figure 1:
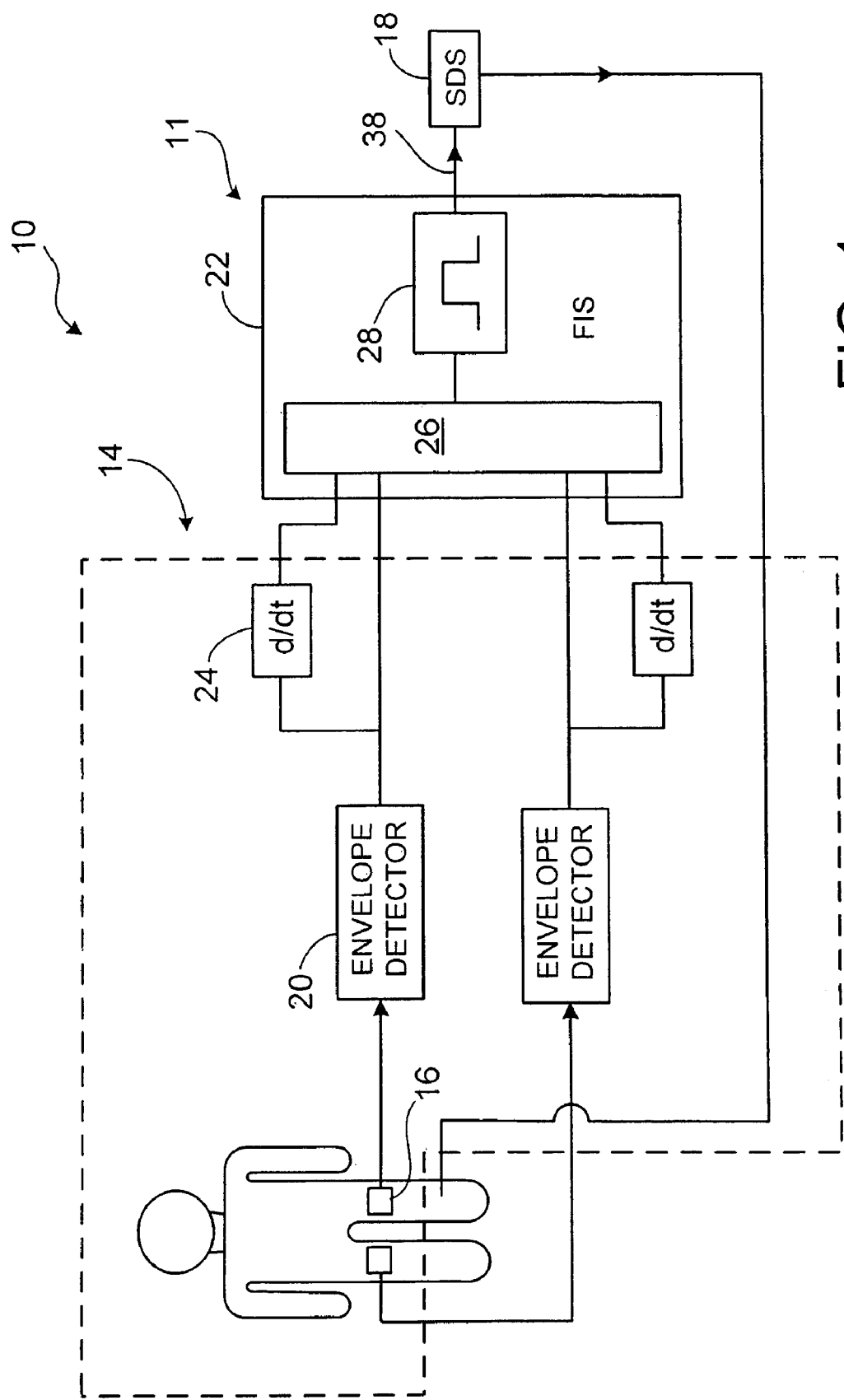
FIGS. 1, 2 and 3 are schematics of a neural prosthesis having a controller for controlling a stimulus delivery system.

A neural prosthesis 10, as shown in FIG. 1, uses electromyographic ("EMG") signals from the upper portion of a leg 12 to identify the onset of particular gait events. This information can then be used to stimulate muscles in the lower portion of the leg, thereby enabling the upper and lower portions of the leg to move together harmoniously.

The exemplary neural prosthesis 10 includes a controller 11 whose function is to identify what the person is doing so that an appropriate control signal can be generated. The controller 11 receives input signals from a signal acquisition portion 14 in electrical communication with nerves that provide signals to the muscles in the upper part of the patient's leg 12, e.g., the quadriceps muscles. The signal acquisition portion 14 includes one or more electrodes 16 implanted into muscles in the upper part of the leg 12. These electrodes 16 receive a signal that provides information about the onset of particular gait events. The information can then be used by the controller 11 to predict the occurrence of a succeeding gait event shortly before it occurs. When provided to a stimulus delivery system ("SDS") 18, the resulting prediction provides a basis for determining when to trigger contraction of muscles in the lower portion of the leg 12 so that the lower portion and upper portions thereof move harmoniously.

The output of the electrodes 16 is provided to an envelope detector 20 to filter out high frequency components that most likely result from noise. The output of the envelope detector 20 is provided both directly to an event model 22 and to a differentiator 24, which provides its own output to an event model 22. In a fuzzy inference system ("FIS") controller 11, a suitable event model 22 is an FIS event model.

The illustrated FIS event model 22 includes a rule base 26 having a Sugeno-type rule for each gait event, and a trapezoidal membership function 28. Signals entering the FIS event model 22 are weighted on the basis of where they fall in a particular trapezoidal membership function 28. The particular shape of a trapezoidal membership function 28 is determined by calibrating the individual patient as described below. The "AND" and "OR" function for operation on fuzzy sets correspond to minimization and maximization respectively. Defuzzification is by weighted average.

The output of the FIS event model 22 provides information on the next gait event and when that event will occur. In FIG. 1, the output of the FIS event model 22 is the control signal provided by the FIS controller 11 to the stimulus delivery system 18. However, the FIS event model 22 lacks memory. As a result, the output of the FIS controller 11 is determined independently of recent gait events. This lack of historical perspective may lead to errors resulting from skipped gait events or gait events occurring in the wrong order. For example, the FIS event model 22 may conclude that the next gait event is to be a mid-stance, even though the immediately preceding weight event was a terminal stance. Although this would make no physiological sense, the FIS event model 22 by itself has no way of excluding the possibility. Related to this is the fact that the FIS event model 22 has no inherent time-sensitivity. As a result, if the FIS event model 22 takes too long to classify an event, there is no way to force it to come to a conclusion promptly.

Figure 2:
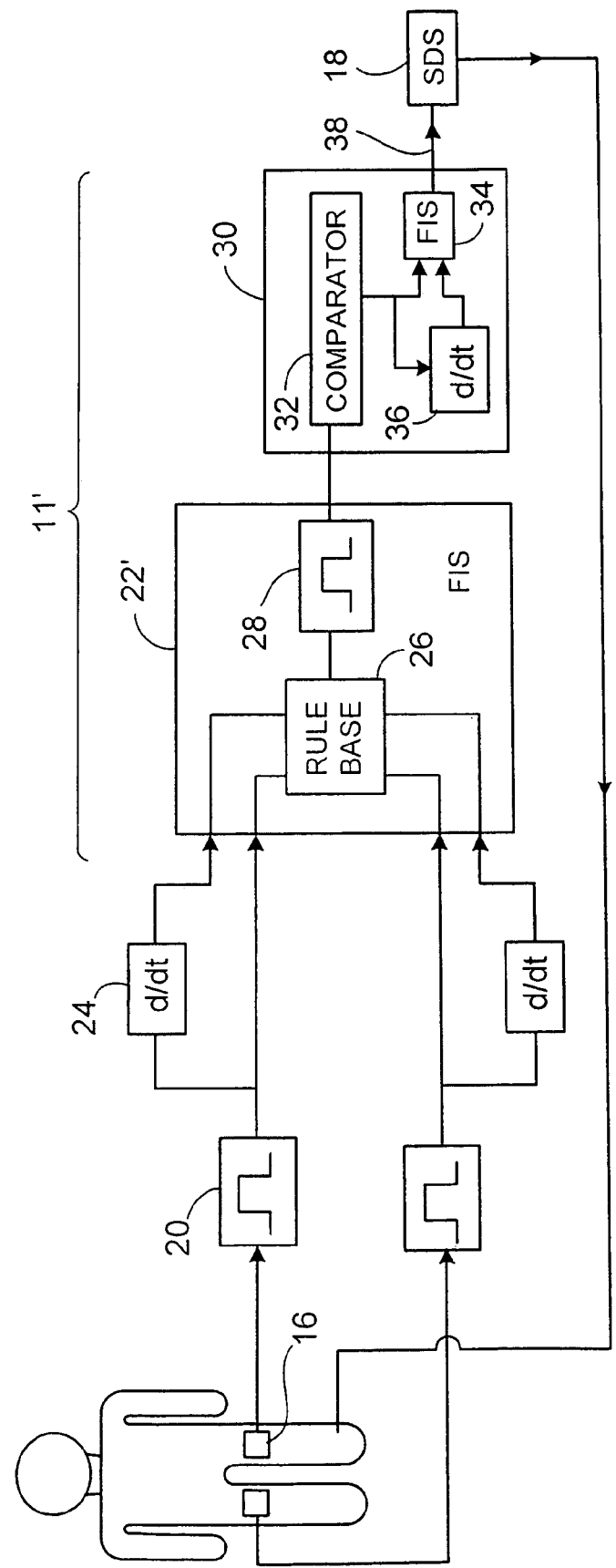

To circumvent these difficulties, an augmented FIS controller 11' includes a supervisory controller 30, as shown in FIG. 2, for further processing the output of the FIS event model 22. The supervisory controller 30 includes a single-step comparator 32 that applies three rules to the next predicted gait event. First, the single-step comparator 32 applies the rule that gait events cannot progress backward. Second, the single-step comparator 32 applies the rule that all events must be in sequence. In other words, there are to be no missed gait events. The final rule ensures that the output of the controller 11 corresponds to one of the predefined events. Thus, intermediate values between events are not allowed. Nor can output values exceed an allowed range, i.e., it is not possible to generate more than the defined number of events.

The output of the single-step comparator 32 is provided both to an additional Sugeno FIS model 34 and to a differentiator 36, an output of which provides a derivative to the additional Sugeno FIS model 34. This additional FIS model 34 accelerates the classification of the model into a gait event, essentially reducing the transition times between gait events.

The output of the additional FIS model 34, which is also the control signal 38 provided by the augmented FIS controller 11', is then provided to the stimulus delivery system 18, which is in electrical communication with a lower muscle of the patient's leg 12. In response to the control signal 38, the stimulus delivery system 18 provides a stimulus to cause the lower muscle of the leg 12 to contract.

Figure 3:
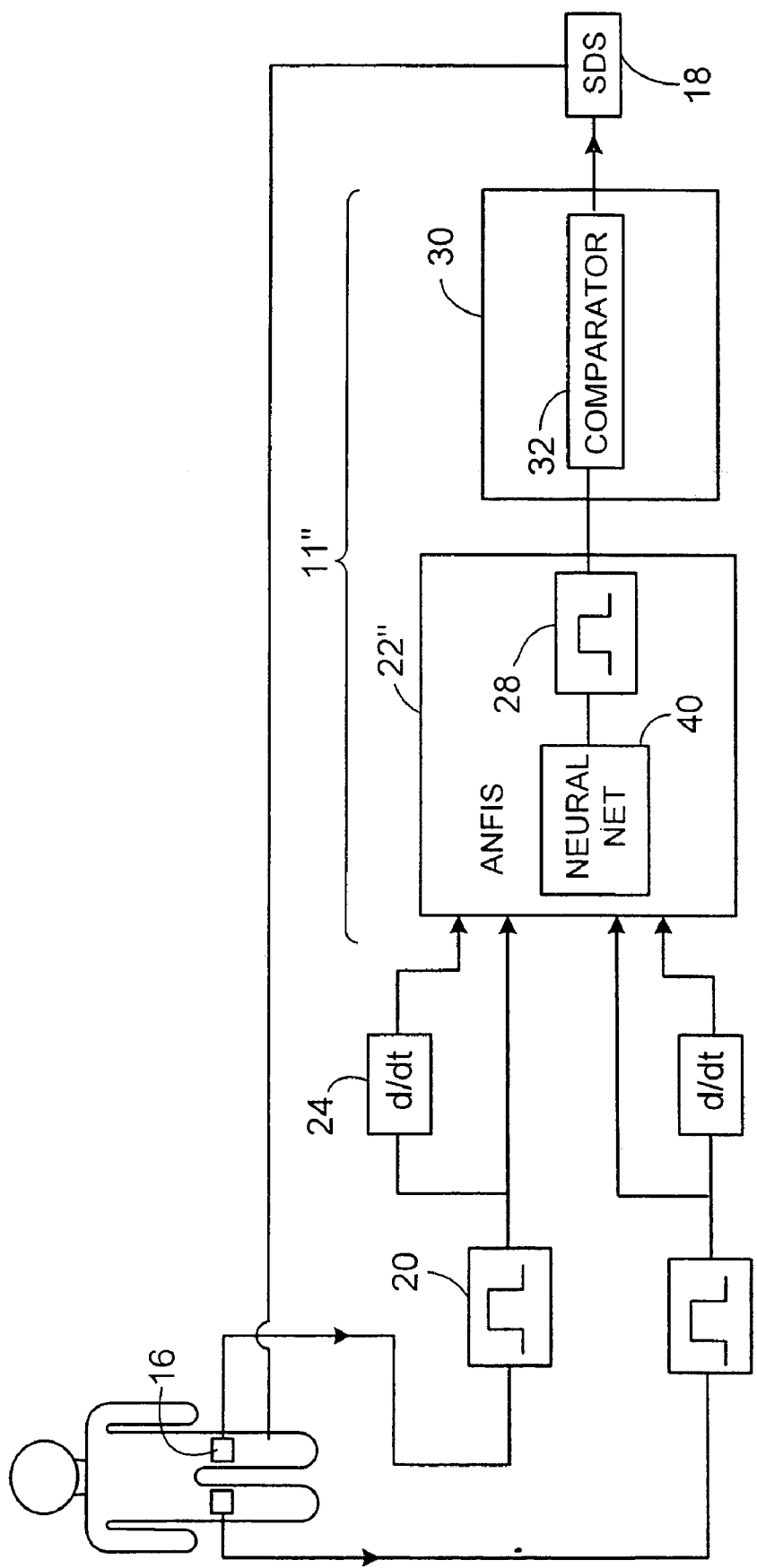

In another embodiment, shown in FIG. 3, the controller is an ANFIS ("Adaptive Neuro-Fuzzy Inference System") controller 11" characterized by an ANFIS event model 22". Unlike the FIS event model 22, an ANFIS event model 22" does not have a rule base. Instead, the ANFIS event model 22" includes a neural net 40 that is trained to classify gait events during a training period. A suitable membership function 28 for the ANFIS event model 22" is a Gaussian function having a spread and center determined by subtractive clustering, as described in more detail in connection with Example II below.

The output of the ANFIS event model 22" is provided to a supervisory controller 30. The supervisory controller 30 implements rules similar to those discussed above in connection with FIGS. 1 and 2. However, the performance of an ANFIS event model 22" is sufficiently stable and accurate such that acceptable results can be obtained without an additional FIS incorporated within the supervisory controller 30.

Stimulus artifacts may occasionally occur in the EMG signal. To avoid such artifacts, sampling rates below 1.2 kHz may be preferable. In an effort to avoid stimulus artifacts, blanking can be introduced and data sets can be re-sampled at lower rates. Experimental results indicate the possibility of effectively using the controller with signal blanking and/or sampling rates at least as low as 200 Hz.

METHOD OF USE

Applications of the ANFIS Controller

An ANFIS controller 11" as described herein can provide a control interface to a stimulus delivery system that will aid in improving the ambulatory ability of those afflicted with cerebral palsy. In this application, the ANFIS controller 11" will use EMG activity from the lower extremity muscles to predict gait events. These predictions can be used to provide appropriate timing for the delivery of electrical stimulation.

The ANFIS event model 22", on its own, generates an unstructured output. As a result, any gait event can be predicted for the output at any given time. There is no memory, and therefore no way to keep track of previous gait event information to determine the plausibility of an output value in the progression of gait events. To improve prediction, a supervisory controller 30 provides a one-point comparison between the previous output of ANFIS event model 22" and its current output. This is effective in structuring the output in a manner that is acceptable for FES control, and doing so at a minimal computation cost.

The ANFIS event model 22", when used in cooperation with the supervisory controller 30, results in an ANFIS controller 11" robust enough to overcome step-to-step variations in the EMG signal and to predict gait events well beyond the number steps that it is trained for. Finally, with the use of the EMG signal as an input, there exists the possibility of implanting the recording electrodes and the connecting wire, thereby improving the cosmesis of these systems and reducing the need for repair and maintenance.

In some cases, artifacts in the EMG signal may affect the ability of the ANFIS controller 11" to predict gait events. Many techniques already exist for removing such artifacts from an EMG signal, primarily by blanking the interval in which the artifact occurs in the EMG recording. If it is assumed that the frequency of electrical stimulation to the lower extremity muscle will be at a minimum of 20 Hz, this will leave a 30 millisecond interval between pulses during which information can be acquired. Given the sampling rate used in this detection scheme (300 Hz), this gives 8 to 9 samples of input data between stimuli, which should be sufficient to extract the control signal. However, if stimulation frequencies increase, there is the possibility that there will be too few data samples between muscle stimuli to predict gait events. In this case, the number of predicted gait events can be reduced. Alternatively, an external sensor source can be used to assist in gait event prediction, or other signal processing methods besides blanking can be applied to remove artifacts. The ANFIS controller 11" described herein samples the EMG at 300 Hz. This value may not be practical for a system with limited data transfer rates. If adequate sampling rates cannot be maintained, the solution may again be to reduce the number of gait events detected, to simplify the membership functions, or to use other sensors, in addition to the EMG to provide inputs to the ANFIS controller 11".

The invention is further described in the following examples, which do not limit the scope of the invention defined by the claims.

EXAMPLE I

One 14 year old (subject 1) female and one 12 year old female (subject 2), both afflicted with spastic diplegia cerebral palsy, were implanted with bifilar percutaneous intramuscular recording electrodes bilaterally. Subject 1 had electrodes implanted into her left rectus femoris and right vastus medialis. Subject 2 had electrodes implanted into her vastus medialis bilaterally. For both subjects, the electrodes' leads were tunneled under the skin to an exit point on the proximal inner thigh for connection to the amplification circuitry. The quadriceps muscles were selected based upon several criteria using pre-study surface EMG recordings collected during several walking trials. Based upon visual inspection, the EMG patterns for these muscles appeared to be of sufficient amplitude and were repeatable from step-to-step. Also, for both subjects, the EMG pattern from one quadriceps appeared to be out of phase with the EMG pattern of the other quadriceps on the opposite leg. This was expected to provide sufficient information content to extract all relevant gait event information.

Intramuscular EMG Recording Electrodes

The bifilar percutaneous electrodes used for this study included two multi-strand 316L stainless steel wires insulated in fluropolymer and wound in a double helix configuration around a polypropylene core. A barb at a distal end of the core ensured anchoring in the muscle tissue. The ends of the stainless steel wire were cleared of insulation and separated by approximately four millimeters to form a bipolar recording configuration.

EMG Signal Acquisition and Processing

Motion Lab System's MA-310® EMG pre-amplifiers were used. These preamplifiers have a gain of 20 and a 3 dB bandwidth from DC to 2 kHz. The amplified signals provided by the pre-amplifiers were connected to a patient-worn backpack unit that provided an anti-alias filter (350 Hz) and a bandpass filter with a passband from 20 to 2,000 Hz. The backpack provided an amplitude turn dial that was adjusted to give maximum gain within the specifications of the analog-to-digital converters (rails are +/−2VDC). The EMG signals were then sampled at 1,200 Hz. Off-line, the signals were full wave rectified and low-pass filtered using a 2nd order Butterworth filter with a cutoff frequency of 1 Hz. The resultant signal, which was a linear envelope of the original signal, served as the input to the fuzzy inference system.

Fuzzy Inference System (FIS)

The amplified and bandpass-filtered intramuscular EMG signals were collected synchronously with kinematic data representing three-dimensional motions of the knee and ankle. The kinematic data was obtained using a limited reflective marker set in conjunction with a VICON® motion-analysis system (Vicon Motion Systems Inc., Lake Forest, Calif.). Five separate trials of two to four steps each were collected on the same day. Sagittal plane kinematic data was used to establish the transitions between the gait phases for each leg. The raw EMG signals as described here were processed as described earlier before being passed into the FIS event model 22.

The fuzzy inference system event model 22 was created using MATLAB® software provided by The Mathworks Inc., Natick, Mass. using the processed EMG signals, their derivatives, and actual gait event data from the first of the five walking trials. Five rule sets were developed, one for each gait event. Rules for only one leg were developed in this initial study. Membership functions were limited to triangular and trapezoidal shapes, and the Sugeno method was used to determine the output. Techniques for creating an FIS event model 22 are described in *Fuzzy Logic Toolbox, User's Guide*, published by The Mathworks, Inc., Natick, Mass., 1995, the contents of which are herein incorporated by reference in their entirety.

Supervisory Controller

When used alone, the FIS event model 22 presented two difficulties. First, the FIS event model 22 had no memory, and therefore was susceptible to output transients that were unrelated to gait. Second, the FIS event model 22 was insensitive to time, and therefore would not force the output into one event or another if the model were taking too long to classify. Since timing is essential in gait control, this was undesirable.

To circumvent these difficulties, the output of the FIS event model 22 was provided to a supervisory controller 30. The supervisory controller 30 included a single-step comparator 32 for applying if-then rules to the output of the FIS event model 22. These rules were structured to suppress transients and oscillations generated by the FIS event model 22. The supervisory controller 30 also included its own Sugeno FIS event model 34. This model operated using the output of the single-step comparator 32 and the derivative of that output to accelerate the prediction of the gait event, essentially reducing the transition times between gait events. To reduce computation time, the membership functions used in this second FIS event model 34 were selected to be trapezoidal.

Controller Analysis

For both subjects, the predictions made by the FIS controller 11 and the augmented FIS controller 11' were evaluated on all trial steps subsequent to the first five used to develop the controller. Performance was evaluated using the techniques disclosed by Williamson, "Gait Event Detection for FES using Accelerometers and Supervised Machine Learning," *IEEE Trans. Rehab. Eng.* 2002, 8:312-319, the contents of which are herein incorporated by reference in their entirety.

The predictions, once classified into appropriate gait events using the VICON® measurements, were examined on a sample-by-sample basis and classified into one of three categories. Correct samples were those in which the controller output matched the VICON data. Transition samples were those in which the controller output indicated transition between consecutive gait events in the natural progression of gait events. Erroneous samples were those samples that would have resulted in the failure of the system as a controller. These could either be short transients between gait events that did not coincide with the natural progression, a backward progression of gait events, or a failure to classify a gait event entirely. The number of samples falling into each category was represented as a percentage determined by the number of samples in a given category out of the total number of samples in a given gait event. Further analysis of the transition state was performed by measuring the time interval between the occurrence of the actual gait event, as measured by the VICON system, and the predicted occurrence of the gait event, as predicted by the controller. Positive time values indicated a prediction that was too early, while negative values indicated a prediction that was too late.

Results

Figure 4:
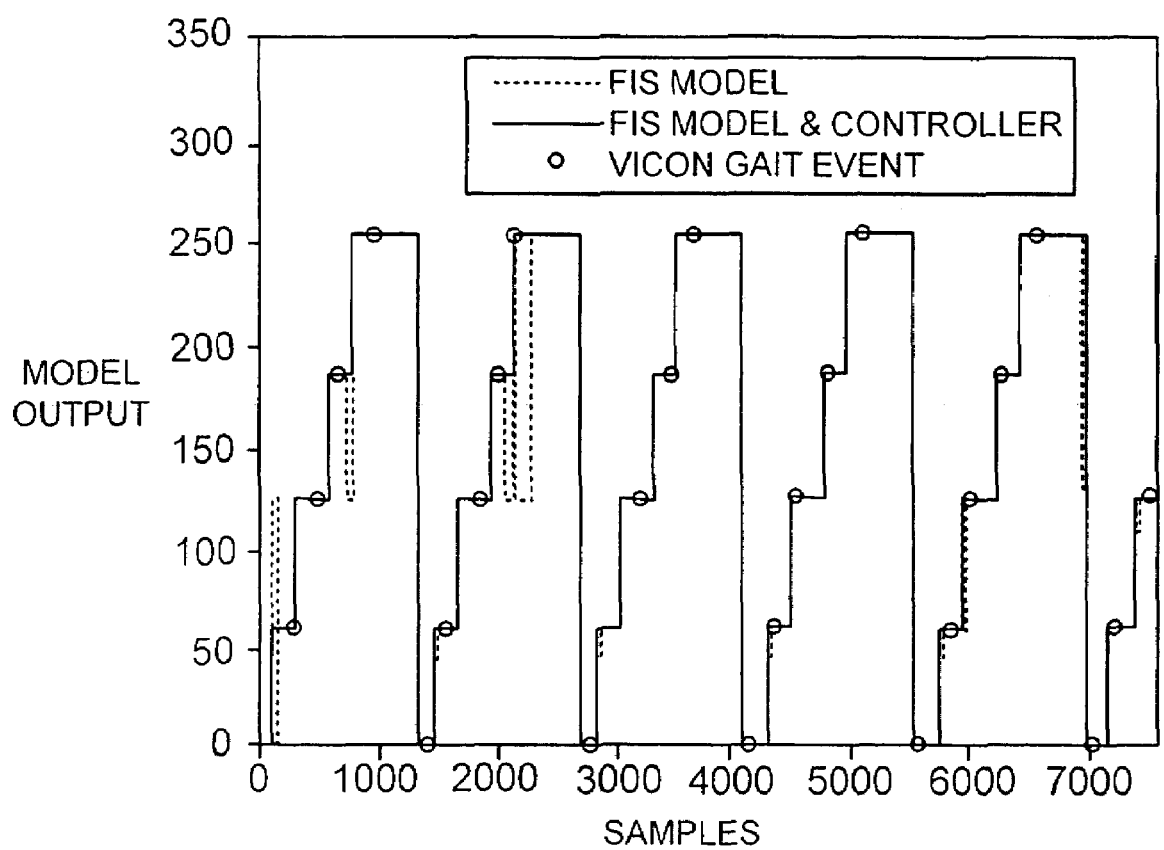
FIG. 4 is a chart showing the performance of the controllers of FIGS. 1 and 2.

The ability of the FIS controller 11 to predict gait events as measured by the VICON system is shown graphically for one subject in FIG. 4. Also represented in the figure are the changes in the output introduced by the application of the supervisory controller 30 in the augmented FIS controller 11'. As can be seen in the figure, both the FIS controller 11 and the augmented FIS controller 11' did an adequate job in predicting the occurrence of a gait event (shown in the figure by the round marker). However, it is also apparent that the supervisory controller 30 improved classification of gait events by removing oscillations and transients in the output of the FIS event model 22, and reducing the transient times between gait events. These findings are more clearly illustrated in the table shown in FIG. 5.

FIG. 5 shows the ability of both the FIS controller 11 and the augmented FIS controller 11' to correctly classify each of the gait events for both subjects across all steps. The values given in FIG. 5 are the averages for each gait event, taken over 51 steps for Subject 1 and over 38 steps for Subject 2. By itself, the FIS event controller 11 classified gait events with error rates less than eight percent for eight of the ten gait events evaluated (see errors in columns labeled "FIS" in FIG. 5). When the augmented FIS controller 11' was used, the error percentages for each subject were further reduced (see errors in columns labeled "FIS+controller" in FIG. 5). For Subject 1, the error percentage was reduced from 0.9%, 3%, and 4.2% to 0% in three out of the five gait events, and from 3.8% and 3.2% to less than 0.3% for the remaining two gait events. For Subject 2, the errors were reduced from 1.7%, 1.2%, and 7.3% to less than 0.3% for three of the gait events, from 14.7% to 7.4% for mid-stance and from 33.9% to 22% for weight acceptance. For both subjects, the supervisory controller 30 also reduced the number of transition points by up to one third on average.

FIG. 6 shows the time interval between the actual gait event and those predicted by the FIS controller 11 and the augmented FIS controller 11'. Both controllers 11, 11' predicted the gait event to occur within 82 milliseconds of its actual occurrence as measured by the VICON system for nine of the ten events evaluated. No significant change in the range or standard deviation was noticed between the FIS controller 11 and the augmented FIS controller 11' for both subjects. However, the cooperation of the supervisory controller 30 in the augmented FIS controller 11' did appear in some cases to cause gait events to be predicted earlier than those derived by the use of the FIS event model 22 controller alone.

Discussion of Results

For both subjects, each gait event was predicted with an accuracy rate of over 80%. In seven of the ten cases, the accuracy rate approached or reached 100%. Because of the nature of the Sugeno fuzzy logic model and the use of trapezoidal membership functions 28 in the FIS event model 22, these accuracy rates were achieved with minimal computation time. The introduction of the supervisory controller 30 increased computation time by placing a one-sample delay in the output of the augmented FIS controller 11'. However, given the sample rate of the EMG signal, this corresponded to a delay of less than one millisecond.

In all cases, the output of the controller 11, 11' predicted that the gait event would occur within 82 milliseconds of when the actual gait event occurred in nine of the ten events evaluated over two subjects. The timing values for the model also indicated that in most cases the model was predicting the occurrence of the gait event before that gait event actually occurred. This is desirable for control of stimulus delivery systems 18 because of the delay between the time a muscle is stimulated and the time it reaches its maximum contracting force. The advance warning of a gait event provided by the controller 11, 11' would permit stimulating a muscle far enough in advance to enable it to achieve the desired contraction just as it is put into use.

assistance to walking with the use of an assistive device. The subjects in this study ranged between a Level I to a Level IV on the Gross Motor Function Classification Scale (GMFCS). This scale is based upon self-initiated movement with an emphasis on trunk control and walking.

Table 1, shown below, summarizes the subjects, the locations of the electrodes, and the number of steps examined for each subject:

TABLE 1

| Subject | Sex | Age | GMFCS | EMG electrode | Muscle | # of steps examined |
|---|---|---|---|---|---|---|
| A | F | 10 | Type I, hemiplegia | Surface | v. lateralis (both) | 32, 12 |
| B | M | 11 | Type I, diplegia | Surface | v. lateralis (both) | 56, 37 |
| C | F | 8 | Type II, diplegia | Surface | v. lateralis (both) | 60, 16 |
| D | M | 9 | Type II, diplegia | Surface | v. lateralis (both) | 65, 42 |
| E | M | 11 | Type II/III, diplegia | Surface | v. lateralis (both) | 53, 33 |
| F | M | 10 | Type IV, diplegia | Surface | v. lateralis (both) | 27, 16 |
| G | F | 18 | Type III, diplegia | Percutaneous | v. lateralis (right) r. femoris (left) | 37 |
| H | F | 11 | Type III, diplegia | Percutaneous | v. lateralis (both) | 51 |

The results presented here were from data collected during several sessions conducted on the same day. Given the fixed location of the recording electrode with respect to the muscle, signal variability related to electrode position would not be expected. However, other issues, such as spasticity and fatigue, could introduce variability in signal amplitude and timing, and thus impact controller performance.

The augmented FIS controller 11' encountered difficulty in correctly classifying weight acceptance for Subject 2 (22% error rate). It appeared that during weight acceptance, the EMG signal amplitude of the leg accepting weight was very small and inconsistent and that of the opposite leg was non-existent (which was not unexpected). Since the rules that form the basis of the controller 11, 11' are based on amplitude changes, the information content was likely too unreliable at this point to provide consistent classification. Errors could perhaps have been reduced with the application of other rules in the supervisory controller 30.

Conclusion

This study examined the ability of an EMG-based fuzzy logic controller 11, 11' to predict gait events in two subjects afflicted with cerebral palsy. For nine of the ten gait events evaluated, results demonstrated the ability of the controller 11, 11' to predict gait events to within 82 milliseconds on average, as referenced to the VICON motion analysis system. For eight of the ten events, prediction errors were 0.3% or less.

EXAMPLE II

Four female and four male subjects were selected for this study, with the ages of the subjects ranging from 8 to 18 years at the time of data collection (Average age of 10.8±3.0 years). All of the subjects in this study were diagnosed with spastic cerebral palsy, were either hemiplegic or diplegic, and ambulated with various degrees of assistance ranging from no EMG and Gait Data Acquisition EMG data was collected from the subjects using either surface or bifilar percutaneous electrodes. These electrodes were located on or in the right and left vastus lateralis muscle in all subjects, except for Subject G in whom the left rectus femoris muscle was used. In all cases, the EMG signals provided by the muscles were of sufficient amplitude for reliable data collection. The EMG signal for one leg was roughly out of phase with the EMG signal of the opposite leg.

The surface electrodes used were the MA-310® EMG recording electrodes available from Motion Lab Systems, Baton Rouge, La. The electrodes were disposed one quarter of the distance along a line from the fibular head to the anterior superior iliac spine (ASIS). Each electrode was a bifilar percutaneous electrode having two multistrand 316L stainless steel wires insulated in fluropolymer and wound in a double helix configuration around a barbed polypropylene core. The ends of the stainless steel wire were cleared of insulation to form a bipolar recording configuration. The distance between the two uninsulated ends of the wire was approximately four millimeters.

Online processing of the EMG signals was provided by the MA-310 system as configured according to established guidelines for collection of EMG data during gait analysis. All EMG signals were sampled at 1.2 kHz, and pre-amplified with a gain of 20. The amplified signal was passed through a low-pass filter having a 2,000 Hz bandwidth. The pre-amplifiers were connected to a patient-worn amplifier unit that provided additional bandwidth filtering from 20 to 2,000 Hz, and anti-alias filtering with a cut-off frequency of 350 Hz. The gain on the patient-worn amplifier was adjusted so that the amplitude of the output EMG signal was within the specifications of the analog-to-digital converters used. In particular, the amplitude was set to conform to rail voltages within ±2.5 VDC.

The gait patterns for each subject were recorded using the VICON® motion analysis system available from Oxford Medics, in the United Kingdom. The gait data was collected at 60 Hz with markers placed on the foot, shank, and thigh of both legs. Each subject was asked to walk in a straight line at a self-selected pace on level ground six to twelve times, for a total of 27 to 65 steps. The gait data was analyzed off-line using the Bodybuilder (™) software package associated with the VICON system. Using this software, the resolution of the occurrence of any given gait event could be determined to within 17 milliseconds. The sagittal plane kinematic data was used to visually identify the occurrence of each of the seven phases of gait, and correlated with the collected EMG data.

For six of the eight subjects (Subjects A-F), a second data collection session was available with simultaneous surface EMG recordings and gait event data. These sessions were collected approximately two months (66.4±13.7 days) later, and were used to test the robustness of the ANFIS controller 11". The data size of this second data session was smaller than the first, with only five to nine trials available (12 to 42 steps).

ANFIS Detection Algorithm

In the design of the ANFIS controller 11", several factors were taken into consideration. The first was to automate as much of the process as possible, so that no knowledge of the system under study was required to train the neural network 40. Also, the ANFIS controller 11" had to be capable of predicting all gait events with the fewest number of inputs, robust enough to compensate for changes in EMG electrode placement, and able to provide repeatable measurements. Finally, the ANFIS controller 11" had to be fast enough to allow for real-time control.

All signal processing and detection was done using MATLAB® (The Mathworks, Inc., Natick, Mass.). The first three trials (six to eleven steps) from each subject were used to train the ANFIS controller 11"; the remaining trials were used for validation. The EMG signals were re-sampled at 300 Hz, full-wave rectified, and low-pass filtered at 3 Hz using a second-order Butterworth filter with phase correction to create a linear envelope. These signals, and the first derivatives thereof, were used as the inputs to ANFIS controller 11" to predict the seven phases of gait. The derivatives, which were calculated by determining a difference between two time points, provided additional information about the activation state of the EMG signal (i.e., increasing or decreasing amplitude). The phases of gait were predicted for only one leg in each subject, with the understanding that the phase event for the other leg could be determined based on this information.

In the ANFIS model 22, the defuzzification of the input was accomplished using Gaussian-shaped membership functions, given by the following equation:

$$F(x;\sigma,c)=\exp(-(x-c)^2/2\sigma^2)$$

where c set the center of the curve and σ dictated the spread. The fuzzy-inference system base for the ANFIS event model 22" implemented a zero-order Sugeno-type system, dictated by the following rule-base structure:

if x is A and y is B then z=k where A and B are fuzzy sets for the input and k is a clearly defined numeric constant in the output. All "AND" operations were accomplished using a product of the inputs, while the aggregation ("defuzzification") of the outputs was performed using a weighted average.

The selection of the number of membership functions, their respective properties, and the number of rules, was accomplished using a subtractive clustering algorithm. The use of a subtractive clustering algorithm allowed full automation by avoiding use of a priori knowledge about the system being modeled. Membership function definition was based upon the concentrations of data points, or finding cluster centers, with in a given data space, N. Initially, each point ($u_k$) in the data space was considered a likely cluster center, and the density measure ($D_k$) of that point was given by the following equation:

$$D_k = \sum e^{-\alpha\|u_k - u_j\|} \text{ for } j = 1 \text{ to } N$$

where:
$u_j$ are the surrounding data points
$\alpha=4/r_a^2$ for $r_a>0$ ($r_\alpha$ being the radius of influence)
Subsequent definitions of cluster centers ($D'_k$) were based upon finding the next highest density of points after the previous cluster center (and its points) was removed. These were governed by the following equation:

$$D'_k=D'_k-D_p e^{-\beta\|u_k-u_p\|}$$

where:
$u_p$ is the center point of the previous cluster group
$D_p$ is the density function of the previous cluster group
$\beta=4/r_b^2$ for $r_b>0$ ($r_b$ being the squash factor)
For the data set used in this study, the radius of influence was between 0.3 and 0.35, with a squash factor of 1.25. These values were selected since they generated a detection scheme composed of ten to thirty membership functions that classified the data set fully without over-fitting the data or becoming computationally too expensive.

The output of the ANFIS controller 11" was a discrete number representing a gait event of the gait cycle. The output was sequentially numbered from one to seven, with an output of one corresponding to a weight-acceptance gait event and an output of seven corresponding to a terminal-swing gait event.

The output of the ANFIS event model 22" was processed further using a supervisory controller 30 having a one-step comparator 32 with a series of if-then rules to structure the output into a control algorithm. There were three rules in the supervisory controller 30. The first rule prevented gait events from progressing backwards, except for the transition from terminal swing to weight acceptance. The second rule ensured that no gait events were skipped. The final rule was that the output of the ANFIS controller 11" must ultimately be one of the seven gait events.

The ANFIS controller 11" was evaluated for repeatability using the second data set for Subjects A through F. The first six to eleven steps were used to recalibrate the ANFIS controller 11"; the remaining steps were used for testing. This recalibration was deemed necessary due to the variations in the placement of the surface recording electrodes and differences in skin impedance. Recalibration was done using three training epochs and a combined back-propagation method with a mixed least-square of the error. The choice of three epochs provided the best reduction of error in the shortest period of time, and prevented over-fitting of the detection scheme to the data.

Analysis

Analysis of the output of the ANFIS controller 11" was performed by comparing its prediction of gait events with the actual times of those gait events as measured by the VICON system.

For each gait event, a time-differential was calculated by comparing the differential of the occurrence of an event as measured by the VICON system with that predicted by the ANFIS controller 11". A negative value for the time-differential indicated that the ANFIS controller 11" predicted a gait event after it had already occurred. A positive value indicated that the ANFIS controller 11" predicted a gait event before the gait event actually occurred. The overall accuracy rate was determined by summing the number of correct matches between the ANFIS data set and the VICON data set, and dividing by the total number of potential matches.

The repeatability of detection by the ANFIS controller 11" was determined through the use of a paired t-test with equal variances on the time-differential calculated with the ANFIS data set and the time-differential calculated with the VICON data set for all gait events. The confidence interval was set to 0.01, with the null hypothesis that there was no difference between the means.

Results

ANFIS Predictive Capabilities

Figure 7:
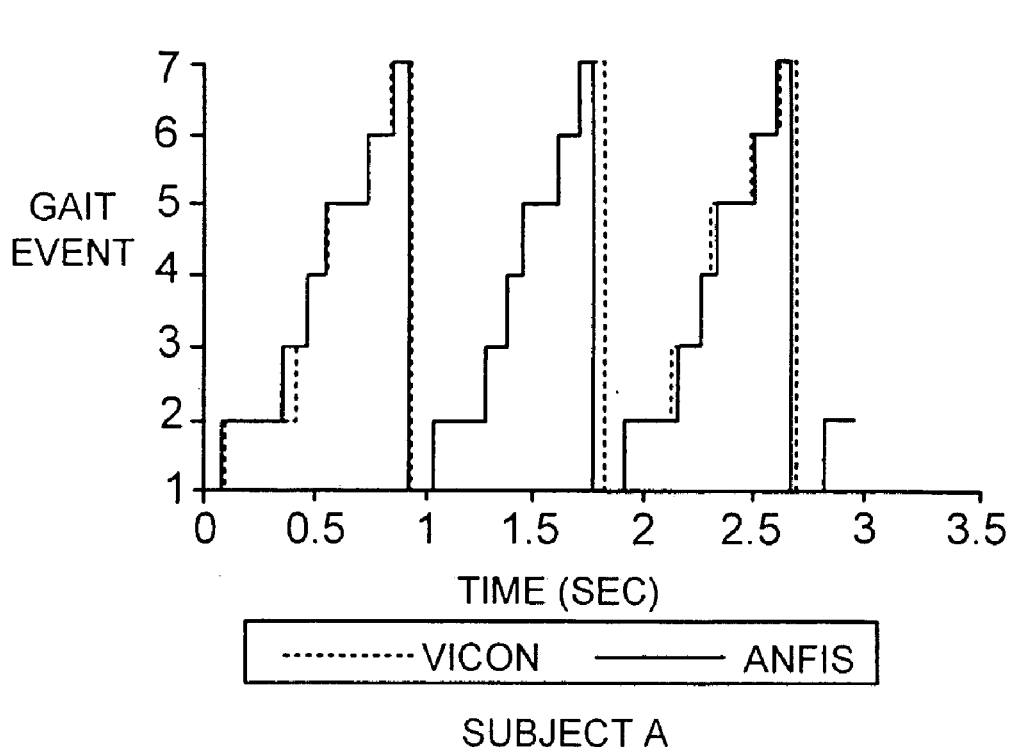
FIG. 7 is a chart showing the performance of the controller in FIG. 3.
Figure 7:
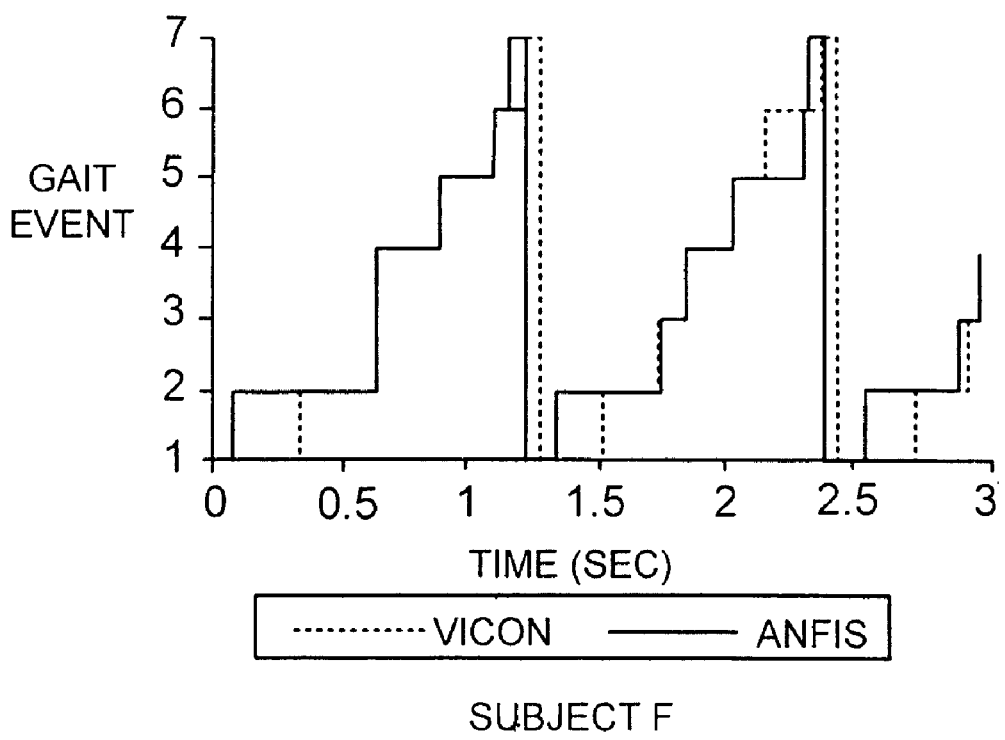
Figure 8:
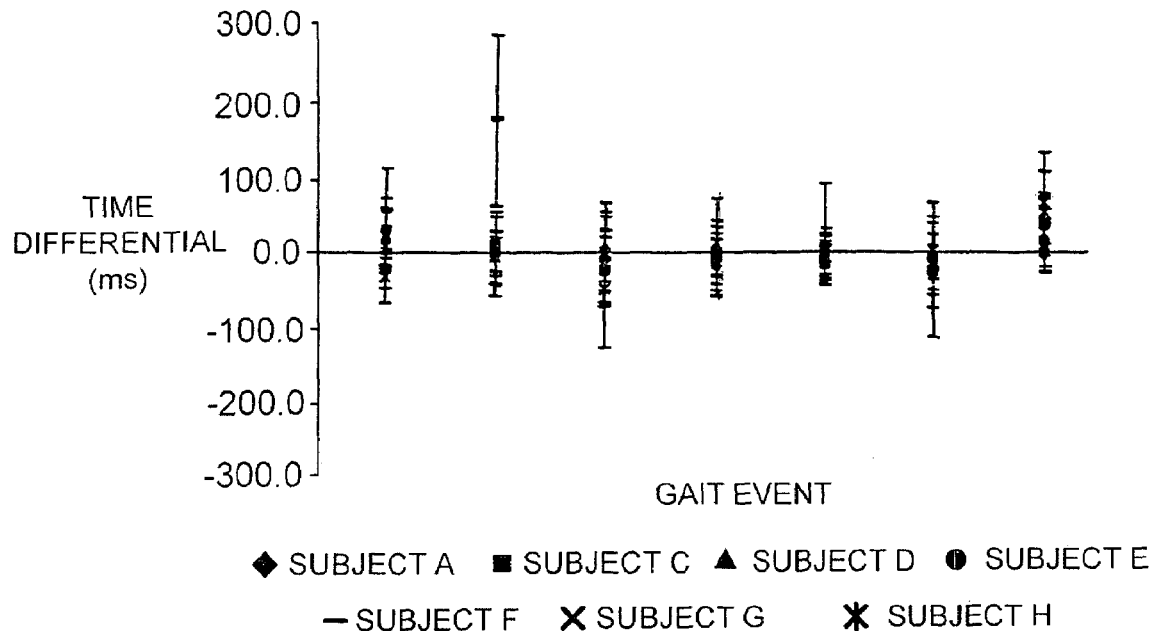
FIGS. 8 and 9 are graphs showing experimental results corresponding to FIG. 7.

FIG. 7 compares ANFIS controller predictions to VICON measurements for subjects A and F. FIG. 8 shows the time-differential calculated between the predictions made by the ANFIS controller 11" and the actual gait event for the first data set associated with each of seven subjects. Also shown in FIG. 8 is the average time-differential calculated across all steps for each gait event in each subject.

Overall, the absolute time-differential between the actual and the predicted event was less than 30 milliseconds, as shown in Table 2:

TABLE 2

| Gait Event | ANFIS (1$^{st}$ set) | ANFIS (2$^{nd}$ set) | p-value (set 1 to set 2) |
|---|---|---|---|
| WA | 4 (40) ms | 18 (38) ms | <<0.001 |
| MSt | 16 (64) ms | 5 (61) ms | 0.125 |
| TSt | −12 (50) ms | −3 (49) ms | 0.121 |
| PSw | −7 (37) ms | −2 (35) ms | 0.263 |
| ISw | −5 (31) ms | −12 (36) ms | 0.127 |
| MSw | −12 (45) ms | −20 (55) ms | 0.166 |
| TSw | 29 (44) ms | 19 (42) ms | 0.062 |

The largest single subject deviations occurred for Subject F, for whom the time-differential for weight acceptance, midstance, and terminal swing ranged from 50 to 150 milliseconds. Of all the participating subjects, this subject had the greatest level of motor impairment. No other trend was observable in the time-differential based upon either the level of motor impairment or the type of electrode used.

The overall accuracy rate for the ANFIS controller 11" output in comparison to the VICON data using the first data set is shown below in Table 3:

TABLE 3

|  | Data Set 1 | Data Set 2 |
|---|---|---|
| Subject A | 98.6 | 98.7 |
| Subject C | 98.3 | 97.8 |
| Subject D | 97.9 | 97.4 |
| Subject E | 97.7 | 97.9 |
| Subject F | 96.2 | 95.3 |
| Subject G | 98.0 |  |
| Subject H | 98.1 |  |
| Range | 96.2-98.6 | 95.3-98.7 |

In Table 3, subjects are listed in order of increasing motor impairment, from Level I to Level IV GMFCS. Subjects G and H (both Level III) were removed from the order because data for those subjects was collected using percutaneous electrodes and thus properly belonged to a separate category. The overall accuracy rates were highest for the subject with a Level I motor impairment, and decreased slightly with increasing levels of motor impairment. However, in all cases the accuracy rate was 95% or greater. The use of percutaneous electrodes demonstrated the ability to decrease the level of error in the predictive abilities of ANFIS controller 11". However, this difference, when compared to a subject with the same level of motor impairment (Subject E) was small (0.3%).

No ANFIS algorithm could be generated with Subject B. Further attempts to build a detection scheme with this subject using other muscles, such as the rectus femoris, the medial hamstrings, the tibialis anterior, and the gastrocnemius, were unsuccessful. Other attempts to add more muscles into the input data set were also unsuccessful.

Repeatability

Figure 9:
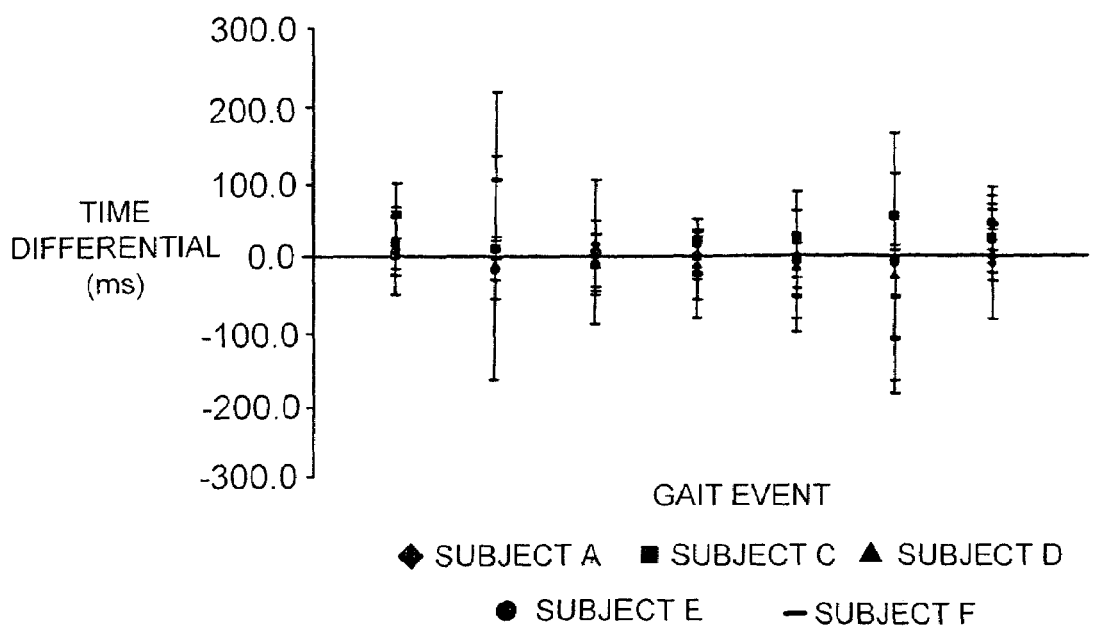

The time-differential results and the overall accuracy rates using the data for the second data set are shown in FIG. 9 and Tables 2 and 3. For all six subjects for which the second data set was available, the ANFIS event model 22" was recalibrated with three epochs, and the ANFIS controller 11" predicted gait events reliably. There was no statistical difference in the time-differentials for all the gait events (Table 3), except for the weight-acceptance event.

The overall time-differential was slightly better with the second data set than it was with the first data set, with the absolute values of the difference being less than 20 milliseconds on average (Table 2). Again, as in the first data set, there was no trend between the level of motor impairment and the values of the time-differential, although Subject F did exhibit the largest deviation from this mean.

ANFIS Algorithm

The gait-event prediction method used an adaptive neuro-fuzzy inference system, or "ANFIS." An ANFIS controller 11" combined the robustness of a fuzzy logic system with the learning abilities of a neural network.

Controller robustness was desirable because of both step-to-step variations in muscle activity and variations arising from other factors that could effect EMG signal generation, such as changes in walking speed, fatigue, and variation in the placement of recording electrodes. The learning abilities of the ANFIS event model 22" allowed for the generation of membership functions and rule bases without any preconceived notions about the data set. In addition, the neural network aspects of the ANFIS event model 22" allowed for multiple attempts at generating the rule base and membership functions. This provided a prediction algorithm that had low gait event prediction error, with the fewest number of rules and membership functions to keep computation times to a minimum.

The ANFIS controller 11" described herein predicted the seven gait events of the gait cycle. However the prediction method is not restricted solely to the prediction of gait events. The seven gait events were selected as being set points throughout the gait cycle and thus would be likely useful for stimulation. It is possible to delineate other events during the gait cycle as long as they are unique and definable. Exemplary events that can be used include events based on maximum and/or minimum values of selected knee angles or ankle angles.

Algorithm Accuracy

The ANFIS controller 11" predicted all seven gait events using two EMG signals and their first derivatives as inputs.

This was accomplished in seven out of the eight subjects studied. For Subject B, attempts to construct an algorithm were unsuccessful, even with the introduction of more input signals (more muscles) or the selection of different input signals (other muscles). Subject B's gait was somewhat variable. He appeared to walk with a medial/lateral sway, as well as a slight crouch that was not apparent in every step. The ANFIS event model 22", while allowing for some vagueness and variability in the input signal, is still based upon neural network techniques that function best when provided with repeatable patterns. This could not be accomplished in the case of subject B.

Excluding the results from Subject B, in all other cases the ANFIS controller 11" adequately predicted all seven gait events, independently of the level of motor impairment. On average, the ANFIS controller 11" predicted the gait event to within 30 milliseconds of its occurrence. With the exception of Subject F, there was no clear trend observable between the level of motor impairment and the magnitude of the time-differential. This subject had the greatest level of motor impairment out of all the subjects examined, and had the largest time-differentials between what was predicted by the controller and the occurrence as measured by the VICON. This time-differential was clearly noticeable in the data set for midstance, and for the terminal stance/weight acceptance transition. However, it should be noted in this case that because of the level of motor impairment the additional difficulty of extracting gait event timing information from the VICON recording may have added to the variability.

The accuracy of the ANFIS controller 11" was also supported by the overall accuracy rate in comparing the algorithm output to the VICON data. The accuracy rates for the first set of data were between 95 to 98%. From the overall accuracy data, a slight trend was observed between the level of motor impairment and the ability of the algorithm to generate an accurate output. There was a slight drop in the accuracy rate with the more involved subjects, however, accuracy rates were still quite high (above 95%). Upon further examination of the data, a vast majority of this error accrued the transition between terminal swing and weight acceptance. The more involved the subject, the less clear the transition between these two phases in the ANFIS controller 11" output became. However, the ANFIS controller 11" did not fail to predict this transition, nor did it miss any of the gait events in any subject.

ANFIS Repeatability

The repeatability of the ANFIS controller 11" was demonstrated in the six subjects where a second data set was available. For these six subjects, following recalibration, the ANFIS controller 11" predicted all seven gait events with time-differentials that were not statistically different from those obtained from the initial data set ($p>0.01$). The only gait event for which this did not hold true was weight acceptance ($p<<0.001$). However, the difference between the time-differentials in this case was below the resolution of the VICON system. Therefore, the differences in this case may not actually have existed, but may have been due to error in predicting gait events from the VICON data set. The recalibration of ANFIS controller 11" was done with the same data size (6 to 11 steps) as was used in the initial training of the neural network 40, and was accomplished using three training intervals, or epochs.

The results of this study demonstrate the feasibility of predicting gait events using surface or intramuscular EMG signals acquired from lower extremity muscles in the child with cerebral palsy. This was accomplished using an ANFIS controller 11" capable of accurately and repeatably predicting gait events and doing so independently of the level of motor impairment.

OTHER EMBODIMENTS

The system and method described herein provide for the application of a fuzzy logic model for real-time prediction of gait events on the basis of EMG signals from lower extremity muscles, thereby enabling the improvement of gait in those afflicted with cerebral palsy by controlling electrical stimulation to the lower extremity.

The present system and method can be implemented using implants, with minimal power requirements from the system. This avoids the difficulties associated with surface mounted devices, such as cosmesis issues, problems with external cabling, which can become entangled or break, and the day-to-day variability associated with the use of externally mounted control systems. However, the present system and method can also be implemented with surface mounted devices to avoid the invasiveness of an implant.

The application of fuzzy logic systems described herein can readily be modified to predict the occurrence of landmark events in other periodic activities. The output of the system can then be provided to a stimulus delivery system to appropriately stimulate muscles that assist in executing the following event. For example, the output of a fuzzy logic system can be used to stimulate upper extremity motion, to control bladder function, and to stimulate and pace respiratory functions. Although useful for persons afflicted with cerebral palsy, systems as described herein can also be useful in connection with persons having other neuromuscular difficulties, for example stroke victims, and persons who have had complete or incomplete spinal cord injury.

The system can also be used for activity based rehabilitation, or wherever there is a desire to reliably predict landmark events in a repetitive motion and to deliver electrical stimulation at times dictated by the occurrence of those events.

As described herein, the inputs to the controllers 11, 11', 11" are EMG signals. However, inputs can arise from sensors placed external to the body. For example, sensors that indicate joint position, linear velocity, or angular velocity can be used to provide input to the fuzzy logic system. So too can external sensors such as foot switches, accelerometers, and goniometers be used. Or, the signals can come from another biological process, for example brain activity. Exemplary signals include electroencephalographs, electrocorticograms, or signals indicative of neural firing rates.

The system described herein can also be modified for multitask use. For example, the system can control gait associated with specialized forms of walking other than walking on level ground. Examples can include walking up and down ramps, or climbing or descending stairs, hopping, skipping, running, and the like.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A neural prosthesis for providing a signal indicative of a predicted event from a cycle of events, the neural prosthesis comprising:
   a signal-acquisition system for receiving a neural signal;
   a first fuzzy-logic inference system for receiving, from the signal acquisition system, a signal indicative of a current location within the cycle of events, the fuzzy-logic inference system being configured to predict a successive event in the cycle of events;

a supervisory controller for receiving an output of the fuzzy-logic inference system, the supervisory controller including a memory for storing data indicative of at least one preceding predicted event in the cycle of events, and a comparator to impose constraints on the successive event at least in part on the basis of the preceding predicted event; and a second fuzzy-logic inference system configured to provide, at least in part on the basis of an output received from the comparator, a signal indicative of a predicted event.

2. The neural prosthesis of claim 1, wherein the comparator is configured to implement a rule requiring that the successive event be selected in a manner consistent with an order of events in the cycle.

3. The neural prosthesis of claim 1, wherein the comparator is configured to implement a rule requiring that the successive event be consistent with a preceding event of the cycle.

4. The neural prosthesis of claim 1, further comprising a stimulus delivery system in communication with the second fuzzy-logic inference system, the stimulus delivery system configured to generate a stimulating signal at least in part on the basis of a signal indicative of a predicted event.

5. The neural prosthesis of claim 1, wherein the signal-acquisition system comprises electrodes for receiving an electro-myographic signal.

6. The neural prosthesis of claim 5, wherein the electrodes comprise surface mounted electrodes.

7. The neural prosthesis of claim 5, wherein the electrodes comprise implantable electrodes.

8. The neural prosthesis of claim 1, wherein the first fuzzy inference system comprises a Sugeno type system.

9. The neural prosthesis of claim 1, wherein the second fuzzy logic inference system comprises a Sugeno type system.

10. The neural prosthesis of claim 1, wherein the first fuzzy inference system comprises an adaptive neuro-fuzzy inference system.

11. A neural prosthesis for providing a signal predicting a successive gait event, the neural prosthesis comprising:

a signal-acquisition system for receiving a neural signal;

a first fuzzy-logic inference system for receiving a signal from the signal acquisition system, the first fuzzy-logic inference system being configured to predict a candidate successive event at least in part on the basis of the signal;

a supervisory controller for receiving data indicative of the candidate successive event from the first fuzzy-logic inference system, the supervisory controller comprising a memory for storing data indicative of a preceding predicted gait event provided by the first fuzzy-logic inference system; and a comparator to impose constraints on a successive gait event at least in part on the basis of the preceding predicted gait event;

a stimulus delivery system in communication with the supervisory controller, the stimulus delivery system being configured to generate a stimulating signal at least in part on the basis of the signal indicative of the predicted event; and a second fuzzy-logic inference system configured to provide, at least in part on the basis of an output received from the comparator, a signal indicative of a predicted event.

12. The neural prosthesis of claim 11, wherein the first fuzzy-logic inference system comprises an adaptive neuro-fuzzy inference system.

13. In a neural prosthesis, a method for providing a signal indicative of a predicted event from a cycle of events, the method comprising:

receiving a neural signal indicative of a current location within the cycle of events;

applying a fuzzy-logic inference algorithm to the neural signal;

storing data indicative of at least one preceding predicted event in the cycle of events;

identifying a constraint on the basis of the preceding predicted event;

imposing the constraint on the successive event;

receiving an output indicative of the successive event following imposition of the constraint thereon; and applying an additional fuzzy-logic algorithm to provide a signal indicative of a predicted event.

14. The method of claim 13, further comprising predicting a successive event in the cycle of events on the basis of an output of the fuzzy-logic inference algorithm.

15. The method of claim 13, wherein identifying a constraint comprises requiring that the successive event be selected in a manner consistent with an order of events in the cycle.

16. The method of claim 13, wherein identifying a constraint comprises requiring that the successive event be consistent with a preceding event of the cycle.

17. The method of claim 13, further comprising generating a stimulus signal at least in part on the basis of a signal indicative of a predicted event.

18. The method of claim 13, wherein receiving a neural signal comprises receiving an electro-myographic signal.

19. The method of claim 13, wherein applying a fuzzy inference algorithm comprises applying a Sugeno type algorithm.

20. The method of claim 13, wherein applying a fuzzy inference algorithm comprises applying an adaptive neuro-fuzzy inference algorithm.

* * * * *